US010866165B2

United States Patent
Su et al.

(10) Patent No.: US 10,866,165 B2
(45) Date of Patent: Dec. 15, 2020

(54) SYSTEM FOR AUTOMATIC SAMPLING AND DETECTION OF ON-LINE GAS BY HIGH-TEMPERATURE AND HIGH-PRESSURE SIMULATOR AND DETECTION METHOD THEREOF

(71) Applicant: Lanzhou Center for Oil and Gas Resources, Institute of Geology and Geophysics, CAS, Gansu (CN)

(72) Inventors: Long Su, Gansu (CN); Yuhong Yuan, Gansu (CN); Gongcheng Zhang, Gansu (CN); Dongwei Zhang, Gansu (CN); Shengrong Tang, Gansu (CN); Jihui Lin, Gansu (CN)

(73) Assignee: NORTHWEST INSTITUTE OF ECO-ENVIRONMENT AND RESOURCES, CHINESE ACADEMY OF SCIENCES, Lanzhou (CN)

( * ) Notice: Subject to any disclaimer, the term of this patent is extended or adjusted under 35 U.S.C. 154(b) by 190 days.

(21) Appl. No.: 16/163,400

(22) Filed: Oct. 17, 2018

(65) Prior Publication Data
US 2019/0128783 A1 May 2, 2019

(30) Foreign Application Priority Data
Oct. 30, 2017 (CN) .............................. 201711042328

(51) Int. Cl.
*G01N 1/22* (2006.01)
*G01N 33/24* (2006.01)
(Continued)

(52) U.S. Cl.
CPC ......... *G01N 1/2202* (2013.01); *G01N 1/2226* (2013.01); *G01N 30/26* (2013.01);
(Continued)

(58) Field of Classification Search
CPC .... G01N 1/00–02; G01N 1/22; G01N 1/2202; G01N 1/2226; G01N 30/04;
(Continued)

(56) References Cited

U.S. PATENT DOCUMENTS 4,578,356 A * 3/1986 Larter .................... G01N 25/14
436/157
4,606,227 A * 8/1986 Walters .................. E21B 49/00
73/865.6

(Continued)

*Primary Examiner* — Nguyen Q. Ha
(74) *Attorney, Agent, or Firm* — Wayne & Ken, LLC; Tony Hom

(57) ABSTRACT

Disclosed is a system for automatic sampling and detection of on-line gas by high-temperature and high-pressure simulator and a detection method thereof. A vacuum manifold I is successively connected to a pressure controller, a gas-liquid separator, a gas automatic metering collector, a first trace quantitative gas collector, and a mechanical pump. On a vacuum manifold II, a high-low pressure convertor, a second trace quantitative gas collector, a gas transferring device, a heavy oil trap, a filtering trap, and a pressure gage head are connected successively. In the present invention, discharged simulation products, enter an empty gas chromatograph at a normal temperature and a normal pressure after treatment, completing on-line detection of an accumulated gas and a stage gas, and improving accuracy of gas composition measurement.

4 Claims, 2 Drawing Sheets

(51) Int. Cl.
  *G01N 30/26* (2006.01)
  *G01N 30/86* (2006.01)
  *G01N 30/02* (2006.01)
  *G01N 1/10* (2006.01)

(52) U.S. Cl.
  CPC ....... *G01N 30/8658* (2013.01); *G01N 33/241* (2013.01); *G01N 2001/105* (2013.01); *G01N 2001/1075* (2013.01); *G01N 2001/2238* (2013.01); *G01N 2030/025* (2013.01)

(58) Field of Classification Search
  CPC .. G01N 30/18–36; G01N 33/00; G01N 33/24; G01N 33/241; G01N 2001/105; G01N 2001/1075; G01N 2001/2238; G01N 2030/025
  See application file for complete search history.

(56) References Cited

U.S. PATENT DOCUMENTS

| | | | |
|---|---|---|---|
| 5,389,550 A * | 2/1995 | Ishida | G01N 33/241 436/32 |
| 10,712,253 B2 * | 7/2020 | Su | G01N 15/082 |
| 2013/0013209 A1 * | 1/2013 | Zhu | G01N 33/24 702/6 |
| 2015/0212235 A1 * | 7/2015 | Barwise | G01V 99/005 703/2 |

* cited by examiner

SYSTEM FOR AUTOMATIC SAMPLING AND DETECTION OF ON-LINE GAS BY HIGH-TEMPERATURE AND HIGH-PRESSURE SIMULATOR AND DETECTION METHOD THEREOF

CROSS-REFERENCE TO RELATED APPLICATIONS

This application claims to Chinese Application No. 201711042328.X with a filing date of Oct. 30, 2017. The content of the aforementioned application, including any intervening amendments thereto, are incorporated herein by reference.

TECHNICAL FIELD

The present invention relates to the technical field of oil-gas geology, specifically to a system for automatic sampling and detection of on-line gas by high-temperature and high-pressure simulator and a detection method thereof.

BACKGROUND

Simulation experiment technologies, as one of the important means for studying mechanism of thermal evolution of source rocks, stimulate a process of oil and gas generation and evolution for different types of source rocks at a low temperature for a long period of time in the natural world by means of a high-temperature and high-pressure simulator in laboratory at a high temperature for a short period of time.

Source rocks in basins containing oil and gas, under underground conditions of certain temperature, pressure, geological time and so on, will generate oil and gas. Compared with the existence time of human beings, the geological time is too long, usually counted by millions of years, and such geological process cannot be observed or directly measured by human beings. Therefore, utilizing the principle of compensating time with temperature, researchers use a temperature higher than the geological temperature, manual simulation time of 72 hours, and a pressure to replace the geological condition for carrying out a simulation experiment of the source rocks, and measuring amounts of a gas (similar to natural gas) and a liquid (similar to petroleum) generated thereby, to provide experimental data for evaluation on the source rocks, and finally correctly evaluate a hydrocarbon-generating potential of the source rocks and an oil-gas resource quantity. According to different research objects and experiment systems, the simulation experiment technologies can be divided into three types: an open system, a closed system, and a semi-closed system. A high-temperature and high-pressure simulator is a semi-closed system, i.e. generation accompanied by discharging.

As in an experiment system of FIG. 1, a rock sample such as a source rock is placed in a cylindrical sample chamber in FIG. 1, then the cylindrical sample chamber is placed into a cylindrical high-temperature and high-pressure kettle with a bigger diameter, and a lithostatic pressure (ranging 50-160 MPa), a confining pressure (greater than the lithostatic pressure), and a fluid pressure (ranging 0-80 MPa) are applied to the source rock sample in a vertical direction on a high-temperature and high-pressure simulator. The kettle is heated with a heating tube, and under a condition of a certain temperature (ranging 250-550° C.), generally after the simulation experiment is carried out for 72 hours, the source rock sample will generate petroleum and natural gas, and presents a high-temperature and high-pressure state. A hydrocarbon discharging valve is opened by means of a pneumatic valve, an electromagnetic valve, and an air compressor, and in the high-vacuum system, a simulation products, after being cooled and depressurized by the controller and the gas-liquid separator, are stored in the gas-liquid separator. When a quantitative amount of gas is collected, a valve at a back end of the gas-liquid separator is opened, after the gas is removed of oil (heavy hydrocarbon), water, and dust (a trace amount of solid powder sample is taken out with a high-pressure gas flow) by the gas-liquid separator, the gas is collected by means of a glass dosing tube through a method of saturated salt water drainage, and fed into an inverted glass flask of 50 mL or 100 mL which is sealed with saturated salt water and a rubber plug; then a few milliliters of the gas is extracted from the glass flask with an injector to be injected into a gas chromatograph, for off-line detection of gas composition.

Such device and method only can be used for composition detection, then the use efficiency of the simulator is low, the accuracy and preciseness of the gas composition are not high, and manual control is further needed, resulting in a big amount of labor and a high experiment cost.

SUMMARY

In view of the above technical problems, the present invention provides a system for automatic sampling and detection of on-line gas by high-temperature and high-pressure simulator and a detection method thereof.

A specific technical solution is as follows:

A system for automatic sampling and detection of on-line gas by high-temperature and high-pressure simulator includes an automatic control program system and a vacuum system. The automatic control program system controls the vacuum system. The vacuum system includes a vacuum manifold I and a vacuum manifold II. An outlet conduit of a high-temperature and high-pressure kettle is connected to a front end of the vacuum manifold I through a pneumatic valve. The pneumatic valve is successively connected to an electromagnetic valve and an air compressor. The vacuum manifold I is successively connected to, from a front end to a back end, a pressure controller, a gas-liquid separator, a gas automatic metering collector, a first trace quantitative gas collector, and a mechanical pump. A terminal end of the vacuum manifold I is connected to a high-vacuum six-way valve of a gas chromatograph. The gas-liquid separator is connected to a cold trap. The first trace quantitative gas collector is connected to a first power source. On the vacuum manifold II, from a front end to a back end, a high-low pressure convertor, a second trace quantitative gas collector, a gas transferring device, a heavy oil trap, a filtering trap, and a pressure gage head are connected successively. A terminal end of the vacuum manifold II is connected to a sample introduction port of the gas chromatograph. The second trace quantitative gas collector is connected to a second power source. The gas transferring device is connected to a carrier gas. A terminal end of the vacuum manifold II is connected to a terminal end of the vacuum manifold I, constituting a loop. A back end of the first trace quantitative gas collector on the vacuum manifold I is connected to a back end of the filtering trap on the vacuum manifold II through a vacuum manifold III, constituting another loop.

A detection method of the detection system is as follows: after a simulation experiment is finished, high-temperature and high-pressure simulation products discharged from the high-temperature and high-pressure kettle pass through the pressure controller, the gas-liquid separator, and the cold trap for twice continuous cooling and depressurizing, then after water removal and dust removal implemented by the gas-liquid separator, only gas is left, and the gas enters the gas automatic metering collector, after metering, a trace amount, 2-4 ml, of the gas is extracted by the first trace quantitative gas collector under the effect of the first power source, then the trace amount of gas is pushed into an on-line gas chromatograph for detection, completing composition detection of accumulated gas.

The detection method further includes: during the simulation experiment, a trace amount of the high-temperature and high-pressure simulation products including stage gas intermittently discharged from the high-temperature and high-pressure kettle passes through the high-low pressure convertor, enters the second trace quantitative gas collector, and is also subjected to twice continuous cooling and depressurizing; the trace amount of high-temperature and high-pressure simulation products entering the second trace quantitative gas collector is then removed of oil and dust by the heavy oil trap and is also removed of water by the filtering trap under the effect of the second power source, thereby only a trace amount 2-4 mL of the stage gas is left, and the trace amount of the stage gas then enters the on-line gas chromatograph for detection, completing composition detection of the stage gas; and redundant simulation products including the stage gas then pass through the vacuum manifold II, and finally enter the gas-liquid separator.

According to design of the simulation experiment, during the simulation experiment, the stage gas is discharged multiple times intermittently at regular intervals, and is subjected to multiple times of detection; the composition detection of the stage gas is mainly completed with the vacuum manifold II and the gas chromatograph, and the stage gas should finally enter into the gas-liquid separator through the vacuum manifold I to be stored.

After the simulation experiment is finished, a summation of a gas volume metered with the gas automatic metering collector and a gas volume metered multiple times by the second trace quantitative gas collector during the simulation experiment process is a total gas volume generated in the simulation experiment. All the detection processes are completed in a completely closed high-vacuum system, avoiding intermediate steps and manual factors, thus improving the use efficiency of the simulator and the preciseness of the gas composition.

With the high-temperature and high-pressure simulator on-line gas automatic sample introduction and detection system and the detection method provided in the present invention, the simulation products in a high-temperature and high-pressure state discharged from the high-temperature and high-pressure simulator are cooled and depressurized in the vacuum system, and subjected to oil removal, water removal, and dust removal, and after the gas volume is metered, the gas enters into an empty gas chromatograph at a normal temperature and a normal pressure, achieving on-line gas automatic sample detection, completing the on-line detection of the accumulated gas and the stage gas. All the detection processes are completed in a completely closed high-vacuum system, avoiding intermediate steps and manual factors, thus improving the use efficiency of the simulator and the preciseness of the gas composition, and reducing labors of experiment personnel and experiment cost.

DETAILED DESCRIPTION

A specific structure and a use method of the present invention are described in combination with accompanying drawings.

Figure 1:
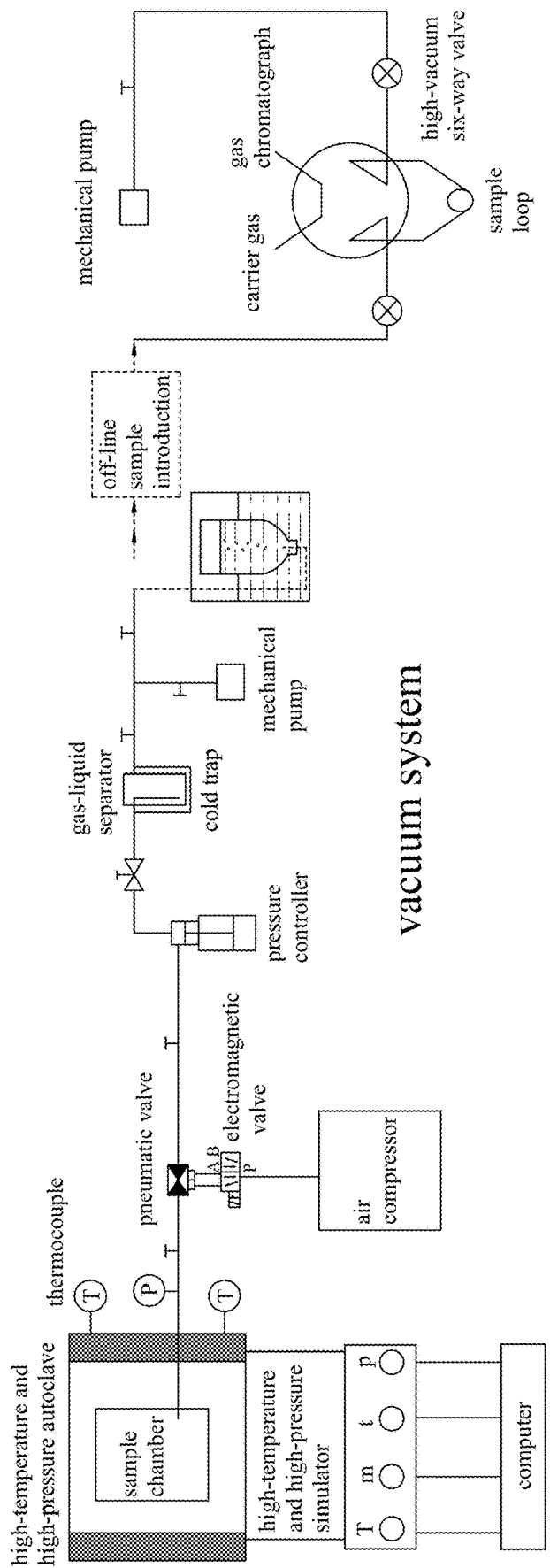
FIG. 1 is a structural schematic diagram according to the prior art.
Figure 2:
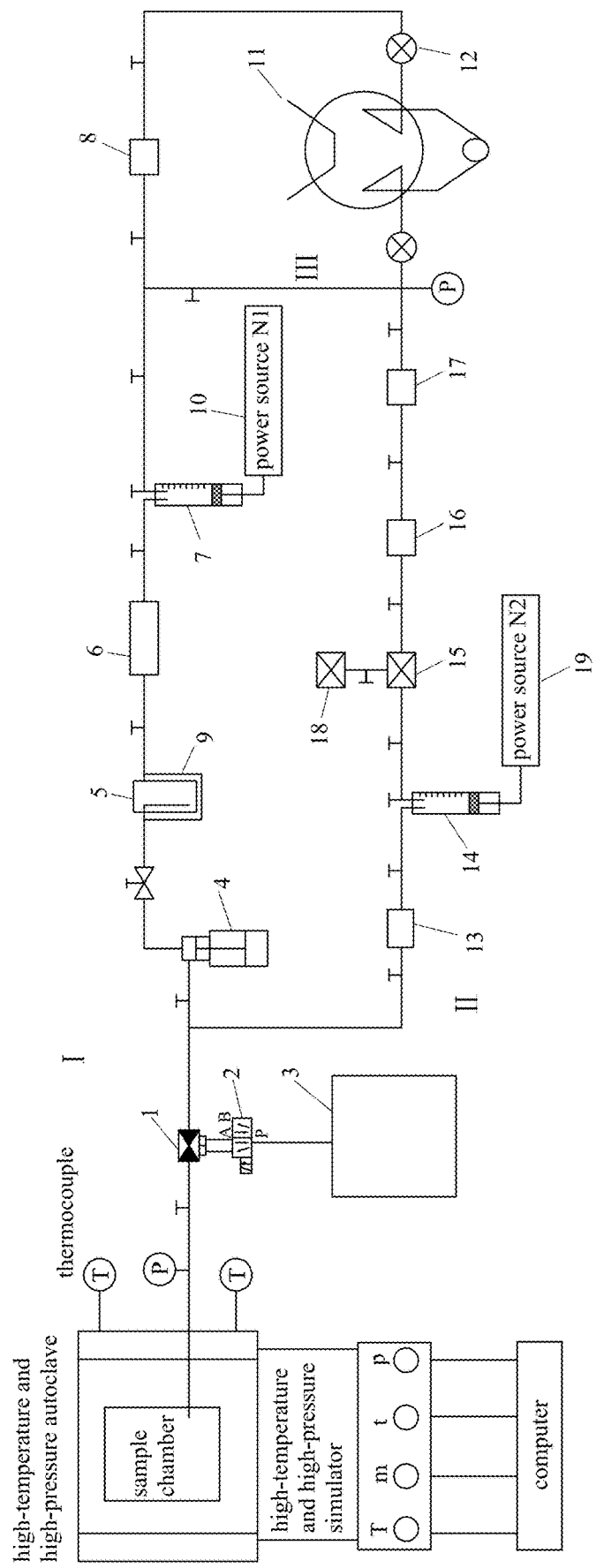
FIG. 2 is a structural schematic diagram according to the present invention.

As shown in FIG. 2, a system for automatic sampling and detection of on-line gas by high-temperature and high-pressure simulator includes an automatic control program system and a vacuum system. The automatic control program system controls the vacuum system. The vacuum system includes a vacuum manifold I and a vacuum manifold II. An outlet conduit of a high-temperature and high-pressure kettle is connected to a front end of the vacuum manifold I through a pneumatic valve 1. The pneumatic valve 1 is successively connected to an electromagnetic valve 2 and an air compressor 3. The vacuum manifold I is successively connected to, from a front end to a back end, a pressure controller 4, a gas-liquid separator 5, a gas automatic metering collector 6, a first trace quantitative gas collector 7, and a mechanical pump 8. A terminal end of the vacuum manifold I is connected to a high-vacuum six-way valve 12 of a gas chromatograph 11. The gas-liquid separator 5 is connected to a cold trap 9. The first trace quantitative gas collector 7 is connected to a first power source 10. On the vacuum manifold II, from a front end to a back end, a high-low pressure convertor 13, a second trace quantitative gas collector 14, a gas transferring device 15, a heavy oil trap 16, a filtering trap 17, and a pressure gage head are connected successively. A terminal end of the vacuum manifold II is connected to a sample introduction port of the gas chromatograph. The second trace quantitative gas collector 14 is connected to a second power source 19. The gas transferring device 15 is connected to a carrier gas 18. A terminal end of the vacuum manifold II is connected to a terminal end of the vacuum manifold I, constituting a loop. A back end of the first trace quantitative gas collector 7 on the vacuum manifold I is connected to a back end of the filtering trap 17 on the vacuum manifold II through a vacuum manifold III, constituting another loop.

A measuring method is as follows: the high-vacuum system is provided with a steel-made pressure controller 4, the gas-liquid separator 5, and the cold trap 9, which continuously perform twice cooling and depressurizing for high-temperature and high-pressure simulation products discharged from the high-temperature and high-pressure kettle after the simulation experiment is finished, and after water removal and dust removal is implemented by the gas-liquid separator 5, only gas is left, and the gas enters the gas automatic metering collector 6. After metering, a trace amount, 2-4 ml, of the gas is extracted by the first trace quantitative gas collector 7 under the effect of the first power source 10, and then the gas is pushed into the on-line gas chromatograph 11 for detection, completing the composition detection of accumulated gas. According to the design of the simulation experiment, after the simulation experiment is finished, such accumulated gas is only subjected to one time of final detection. The composition detection of the accumulated gas is mainly completed with the vacuum manifold I and the gas chromatograph 11.

The vacuum manifold II is provided with a steel-made high-low pressure convertor 13, the second trace quantitative gas collector 14, and the gas transferring device 15. During the simulation experiment, a trace amount of the high-temperature and high-pressure simulation products including stage gas intermittently discharged from the high-temperature and high-pressure kettle, passes through the steel-made high-low pressure convertor 13, enters the second trace quantitative gas collector 14, and is also subjected to twice continuous cooling and depressurizing. The trace amount of high-temperature and high-pressure simulation products entering the second trace quantitative gas collector 14 is then removed of oil (heavy hydrocarbon) and dust (a trace amount of solid powder sample is taken out with a high-pressure gas flow) by the heavy oil trap 16 and is also removed of water by the filtering trap 17 under the effect of the second power source 19, thereby only a trace amount (2-4 mL) of the stage gas is left, and the stage gas then enters the on-line gas chromatograph 11 for detection, completing the composition detection of the stage gas. According to the design of the simulation experiment, during the simulation experiment, such stage gas is discharged multiple times intermittently at regular intervals, and is subjected to multiple times of detection. The composition detection of the stage gas is mainly completed with the vacuum manifold II and the gas chromatograph 11, and the stage gas should finally enter into the gas-liquid separator 5 through the vacuum manifold I, via the vacuum manifold II, to be stored in the gas-liquid separator 5.

After the simulation experiment is finished, a summation of a gas volume metered with the gas automatic metering collector 6 and a gas volume metered multiple times by the second trace quantitative gas collector 14 during the simulation experiment process is a total gas volume generated in the simulation experiment. All the detection processes are completed in a completely closed high-vacuum system, avoiding intermediate steps and manual factors, thus improving the use efficiency of the simulator and the preciseness of the gas composition.

What is claimed is:

1. A system for automatic sampling and detection of on-line gas by high-temperature and high-pressure simulator, comprising an automatic control program system and a vacuum system, wherein the automatic control program system controls the vacuum system; the vacuum system comprises a vacuum manifold I and a vacuum manifold II; an outlet conduit of a high-temperature and high-pressure kettle is connected to a front end of the vacuum manifold I through a pneumatic valve; the pneumatic valve is successively connected to an electromagnetic valve and an air compressor; the vacuum manifold I is successively connected to, from a front end to a back end, a pressure controller, a gas-liquid separator, a gas automatic metering collector, a first trace quantitative gas collector, and a mechanical pump; a terminal end of the vacuum manifold I is connected to a high-vacuum six-way valve of a gas chromatograph; the gas-liquid separator is connected to a cold trap; the first trace quantitative gas collector is connected to a first power source; on the vacuum manifold II, from a front end to a back end, a high-low pressure convertor, a second trace quantitative gas collector, a gas transferring device, a heavy oil trap, a filtering trap, and a pressure gage head are connected successively; a terminal end of the vacuum manifold II is connected to a sample introduction port of the gas chromatograph; the second trace quantitative gas collector is connected to a second power source; the gas transferring device is connected to a carrier gas; a terminal end of the vacuum manifold II is connected to a terminal end of the vacuum manifold I, constituting a loop; a back end of the first trace quantitative gas collector on the vacuum manifold I is connected to a back end of the filtering trap on the vacuum manifold II through a vacuum manifold III, constituting another loop.

2. A detection method of a system for automatic sampling and detection of on-line gas by high-temperature and high-pressure simulator according to claim 1, comprising the following process:

after a simulation experiment is finished, high-temperature and high-pressure simulation products discharged from the high-temperature and high-pressure kettle pass through the pressure controller, the gas-liquid separator, and the cold trap for twice continuous cooling and depressurizing, then after water removal and dust removal implemented by the gas-liquid separator, only gas is left, and the gas enters the gas automatic metering collector, after metering, a trace amount, 2-4 ml, of the gas is extracted by the first trace quantitative gas collector under the effect of the first power source, then the trace amount of gas is pushed into an on-line gas chromatograph for detection, completing composition detection of accumulated gas.

3. The detection method of a system for automatic sampling and detection of on-line gas by high-temperature and high-pressure simulator according to claim 2, further comprising the following process:

during the simulation experiment, a trace amount of the high-temperature and high-pressure simulation products including stage gas intermittently discharged from the high-temperature and high-pressure kettle passes through the high-low pressure convertor, enters the second trace quantitative gas collector, and is also subjected to twice continuous cooling and depressurizing; the trace amount of high-temperature and high-pressure simulation products including the stage gas entering the second trace quantitative gas collector is then removed of oil and dust by the heavy oil trap and is also removed of water by the filtering trap under the effect of the second power source, thereby only a trace amount 2-4 mL of the stage gas is left, and the trace amount of the stage gas then enters the on-line gas chromatograph for detection, completing composition detection of the stage gas; and redundant simulation products including the stage gas then pass through the vacuum manifold II, and finally enter the gas-liquid separator.

4. The detection method of a system for automatic sampling and detection of on-line gas by high-temperature and high-pressure simulator according to claim 3, wherein according to design of the simulation experiment, during the simulation experiment, the stage gas is discharged multiple times intermittently at regular intervals, and is subjected to multiple times of detection; the composition detection of the stage gas is completed with the vacuum manifold II and the gas chromatograph, and the stage gas finally enters into the gas-liquid separator through the vacuum manifold I to be stored.

* * * * *